United States Patent
Brax et al.

(10) Patent No.: US 9,724,199 B2
(45) Date of Patent: Aug. 8, 2017

(54) ORTHOPAEDIC IMPLANT AND METHOD FOR MANUFACTURING SUCH AN ORTHOPAEDIC IMPLANT

(71) Applicants: Michel Brax, Mommenheim (FR); Jean-Louis Charissoux, Limoges (FR); Sébastien Lustig, Lyons (FR); Pascal Maman, Marseilles (FR); Olivier Roche, Ludres (FR); Guillaume Venet, St Martin des Noyers (FR)

(72) Inventors: Michel Brax, Mommenheim (FR); Jean-Louis Charissoux, Limoges (FR); Sébastien Lustig, Lyons (FR); Pascal Maman, Marseilles (FR); Olivier Roche, Ludres (FR); Guillaume Venet, St Martin des Noyers (FR)

( * ) Notice: Subject to any disclaimer, the term of this patent is extended or adjusted under 35 U.S.C. 154(b) by 123 days.

(21) Appl. No.: 14/377,671

(22) PCT Filed: Feb. 19, 2013

(86) PCT No.: PCT/FR2013/050336
§ 371 (c)(1),
(2) Date: Aug. 8, 2014

(87) PCT Pub. No.: WO2013/124577
PCT Pub. Date: Aug. 29, 2013

(65) Prior Publication Data
US 2015/0045904 A1    Feb. 12, 2015

(30) Foreign Application Priority Data
Feb. 20, 2012    (FR) .................... 12 51516

(51) Int. Cl.
*A61F 2/34* (2006.01)
*A61L 27/30* (2006.01)
(Continued)

(52) U.S. Cl.
CPC ............ *A61F 2/34* (2013.01); *A61F 2/30767* (2013.01); *A61L 27/306* (2013.01); *A61L 27/34* (2013.01);
(Continued)

(58) Field of Classification Search
CPC ...................................................... C23C 28/02
See application file for complete search history.

(56) References Cited

U.S. PATENT DOCUMENTS

| 4,542,539 A | 9/1985 | Rowe, Jr. et al. |
| 5,024,670 A | 6/1991 | Smith et al. |

(Continued)

FOREIGN PATENT DOCUMENTS

| EP | 1 647 242 A1 | 4/2006 |
| WO | WO 02/17820 A1 | 3/2002 |

OTHER PUBLICATIONS

Written Opinion of the International Searching Authority issued in International Application No. PCT/FR2013/050336 dated May 29, 2013.
(Continued)

*Primary Examiner* — Thomas J Sweet
*Assistant Examiner* — Megan Wolf
(74) *Attorney, Agent, or Firm* — Oliff PLC

(57) ABSTRACT

This orthopedic implant includes a polymer substrate with an outer surface intended to be secured to a bone tissue. The outer surface is covered with metal particles including titanium. The particles include large primary particles and small secondary particles. The primary particles and the secondary particles are evenly distributed over the outer surface.

18 Claims, 2 Drawing Sheets

(51) Int. Cl.
*A61F 2/30* (2006.01)
*A61L 27/34* (2006.01)
*A61L 27/50* (2006.01)

(52) U.S. Cl.
CPC ............ *A61L 27/50* (2013.01); *A61F 2/3094* (2013.01); *A61F 2002/30013* (2013.01); *A61F 2002/30065* (2013.01); *A61F 2002/30769* (2013.01); *A61F 2210/008* (2013.01); *A61F 2310/00407* (2013.01); *A61L 2400/14* (2013.01); *A61L 2420/04* (2013.01)

(56) References Cited

U.S. PATENT DOCUMENTS

| | | | | |
|---|---|---|---|---|
| 5,405,389 | A * | 4/1995 | Conta | A61F 2/30767 |
| | | | | 623/23.55 |
| 5,795,647 | A * | 8/1998 | Robinson | B41N 1/12 |
| | | | | 427/198 |
| 2006/0116774 | A1 | 6/2006 | Jones et al. | |
| 2007/0191962 | A1 | 8/2007 | Jones et al. | |
| 2012/0041564 | A1 * | 2/2012 | Landon | A61F 2/389 |
| | | | | 623/20.34 |
| 2015/0190232 | A1 * | 7/2015 | Vandevelde | A61F 2/34 |
| | | | | 623/22.21 |

OTHER PUBLICATIONS

International Search Report issued in International Application No. PCT/FR2013/050336 dated May 29, 2013.

* cited by examiner

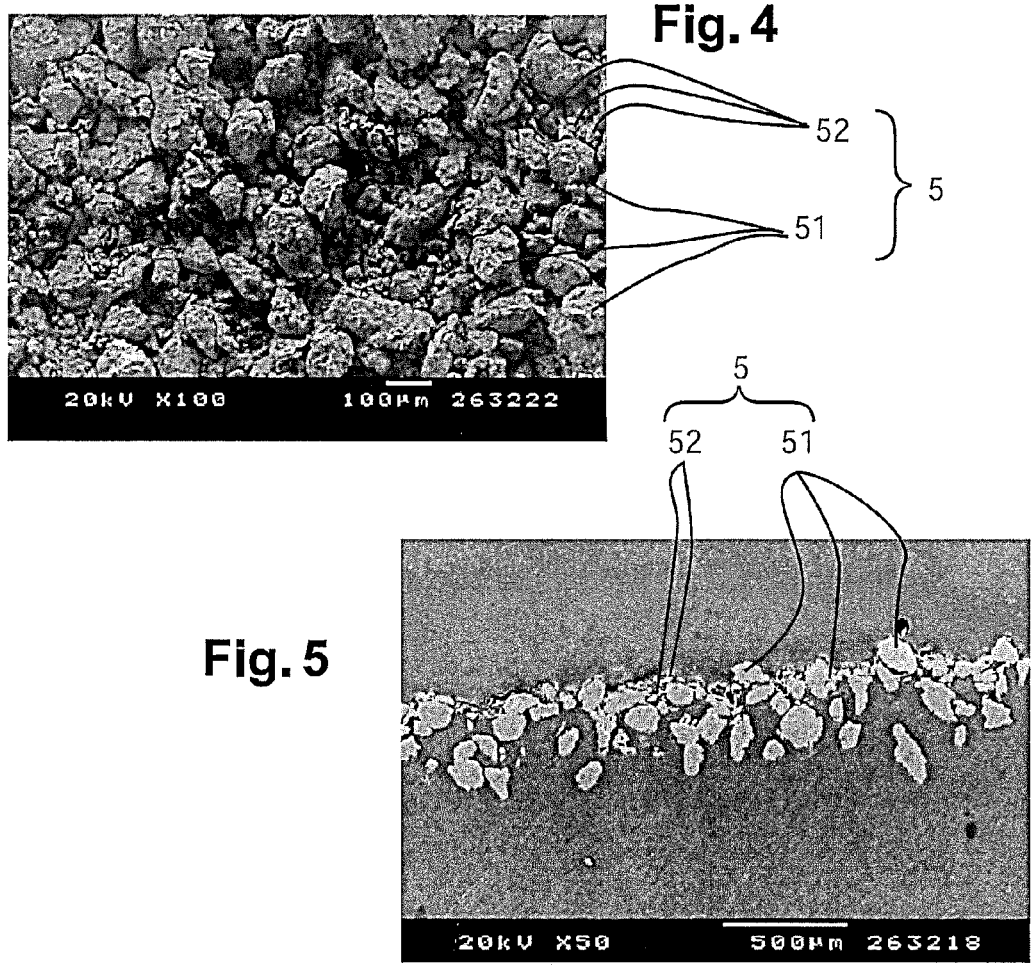
Fig. 4
Fig. 5
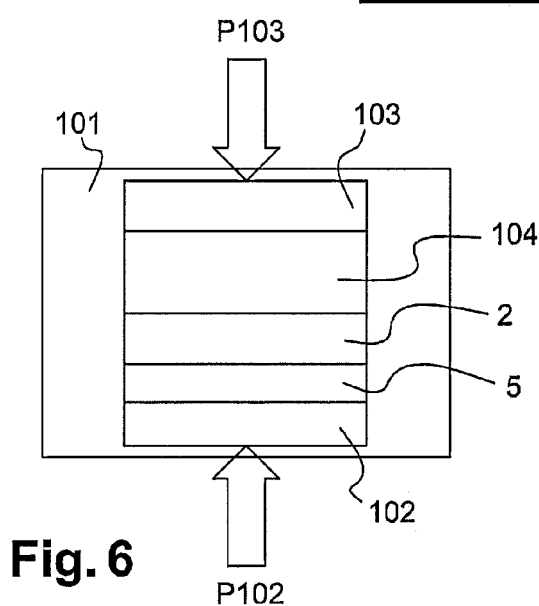
Fig. 6

ORTHOPAEDIC IMPLANT AND METHOD FOR MANUFACTURING SUCH AN ORTHOPAEDIC IMPLANT

The present invention relates to an orthopaedic implant, such as an acetabular cup for hip prosthesis. Moreover, the present invention relates to a method, for manufacturing an orthopaedic implant, such as an acetabular cup for a hip prosthesis.

The present invention finds particularly application in the field of repair surgery and orthopaedics, in particular for the manufacture of hip prostheses.

U.S. Pat. No. 5,024,670 describes an orthopaedic implant and its manufacturing method. The implant includes a polymer substrate having an outer surface intended to be secured to a bone tissue. The outer surface is covered with titanium particles of a relatively large size, because their grain size is comprised between 177 μm and 250 μm.

However, this large size of the titanium particles induces a particles distribution which is not uniform over the outer surface. Indeed, the deposition of these large particles generates interstices of very variable dimensions. Consequently, the ineffective bone growth on such an outer surface performs a bad adhesion of the bone, which reduces the service life of the prosthesis.

The present invention aims in particular to solve, in whole or in part, the above-mentioned problems.

To this end, the invention has for an object an orthopaedic implant, such as an acetabular cup for hip prosthesis, the orthopaedic implant including at least one substrate which comprises at least one polymer plastic material and which has an outer surface intended to be secured to a bone tissue, said outer surface being partially covered with particles of at least one metallic material comprising titanium;

the orthopaedic implant being characterized in that said particles comprise primary particles and secondary particles, the primary particles having a grain size ranging from 180 μm to 600 μm, preferably from 200 μm to 500 μm, the secondary particles having a grain size ranging from 70 μm to 145 μm, preferably from 90 μm to 125 μm, the primary particles and the secondary particles being distributed in a relatively uniform manner over the outer surface.

In other words, the outer surface is covered with small particles and large particles.

Thus, such a covering allows increasing, or even maximizing, the covering rate and the quantity of interstices, hence promoting the bone growth and the adhesion of the bone tissue, which leads to a long service life of the prosthesis.

In the present application, the term "grain size" refers to the size of the particles or "grains". The grain size is usually characterized by a characteristic grain size spectrum of a numeric distribution of the particles of a set according to the dimension of each particle.

According to one alternative of the invention, the outer surface may be partially covered with other particles, metallic or not, and having a distinct grain size, for example intermediate between those of the primary and secondary particles.

Thus, these other particles allow fitting to areas having different bone densities.

According to one embodiment of the invention, said polymeric plastic material is selected in the group consisting of a polyethylene (PE), an ultra-high molecular weight polyethylene (UHMW-PE), a highly cross-linked polyethylene (XLPE), an E-vitaminized polyethylene, a polyurethane and a polyether ether ketone (PEEK).

Thus, such a polymer plastic material allows performing a biocompatible, light and mechanically and chemically resistant substrate.

According to one embodiment of the invention, the or each metallic material is selected in the group consisting of pure titanium, an alloy of titanium, chromium, cobalt and stainless steel such as the 316LVM steel.

Thus, such a metallic material allows promoting adhesion of the bone tissues growing around the outer surface.

According to one embodiment of the invention, the primary particles and the secondary particles are composed of the same metallic material.

Thus, such primary particles and secondary particles can be implemented in the same manner, for example at the same temperature and/or at the same pressure.

According to one embodiment of the invention, the surface area of the outer surface portion that is not covered with said particles represents between 15% and 30%, preferably between 20% and 25%, of the total surface area of the outer surface.

In other words, the covering rate of the outer surface with the metallic material is comprised between 60% and 80%, preferably between 65% and 75%. Thus, such a covering rate allows the adhesion and the growth of many bone tissues, which is not the case when the metallic particles are too small and induce a too high covering rate.

According to one alternative of the invention, the primary interstices between primary particles have approximately equal surface areas.

Thus, such interstices allow implanting smaller secondary particles, which guarantees uniform distributions of the primary and secondary particles over the outer surface. In the present application, the term "approximately equal" indicates for example that the surface areas of the primary interstices vary by more or less 20% relative to their median.

According to one embodiment of the invention, the number of primary particles substantially represents between 5% and 50%, preferably between 10% and 30%, of the sum of the number of primary particles and the number of secondary particles.

The sum of the number of primary particles and the number of secondary particles generally corresponds to the total number of particles.

Thus, such proportions of primary and secondary particles allow performing a dense and uniform bone growth.

As a corollary, the number of secondary particles substantially represents between 95% and 50%, preferably between 70% and 30%, of the sum of the number of primary particles and the number of secondary particles.

According to one embodiment of the invention, the outer surface has generally the shape of a spheroidal portion, preferably the shape of a half-sphere.

Thus, a hemispherical outer surface allows performing an isotropic adhesion, that is to say an adhesion resistant to forces exerted along different directions.

According to one embodiment of the invention, the orthopaedic implant includes a one-piece single substrate.

Thus, such a one-piece substrate is relatively easy to manufacture.

Furthermore, the present invention relates to a method for manufacturing an orthopaedic implant, such as an acetabular cup for a hip prosthesis, the orthopaedic implant comprising at least one polymeric plastic material having an outer surface intended to be secured to a bone tissue, the method comprising the steps of:

heating said outer surface at a softening temperature of the polymer plastic material, the substrate being preferably placed in a mold;

partially covering said outer surface with primary particles of at least one metallic material comprising titanium, the primary particles having a grain size ranging from 180 μm to 600 μm, preferably from 200 μm to 500 μm, the primary particles being distributed in a relatively uniform manner over the outer surface;

pressing a heated die against the outer surface, so as to secure the primary particles to the outer surface;

partially covering said outer surface with secondary particles of at least one metallic material comprising titanium, the secondary particles having a grain size ranging from 70 μm to 145 μm, preferably from 90 μm to 125 μm, the secondary particles being distributed in a relatively uniform manner over the outer surface; and pressing the heated die against the outer surface, so as to secure the secondary particles to the outer surface.

Thus, such a method allows manufacturing an orthopaedic implant in accordance with the invention in a reliable and quick manner. In particular, such a method does not implement plasma deposition, particularly energy-intensive and random.

According to one embodiment of the invention, the step of covering the outer surface with the primary particles is performed before the step of covering the outer surface with the secondary particles.

In other words, the (small) secondary particles complete the locations left vacant by the (large) primary particles.

Thus, such a succession of these steps allows distributing in a particularly uniform manner the primary and secondary particles.

According to one alternative of the invention, the primary particles and the secondary particles are mixed beforehand to form a homogeneous powder, and wherein the step of covering the outer surface with the primary particles is performed simultaneously with the step of covering the outer surface with the secondary particles.

Thus, such simultaneity of these steps allows quickly manufacturing an orthopaedic implant in accordance with the invention.

According to one embodiment of the invention, the step of covering the outer surface with the primary particles and the step of covering the outer surface with the secondary particles are performed by contacting in an enclosed volume which is pressurized and heated at a temperature lower than the melting temperature of the polymer plastic material.

Thus, such a deposition method is quick to perform.

The above-mentioned embodiments and alternatives may be taken separately or according to any technically permissible combination.

The present invention will be well understood and its advantages will also appear in the light of the following description, given only by way of a non-limiting example and made with reference to the appended drawings, wherein:

FIG. 4 is a microscopic photography of a portion of the orthopaedic implant of FIG. 1;

FIG. 5 is a microscopic photography, to half the scale of FIG. 4, of a portion of the orthopaedic implant of FIG. 1; and FIG. 6 is a schematic view illustrating a step of a method in accordance with the invention, for manufacturing the orthopaedic implant of FIGS. 1 to 5.

Figure 1:
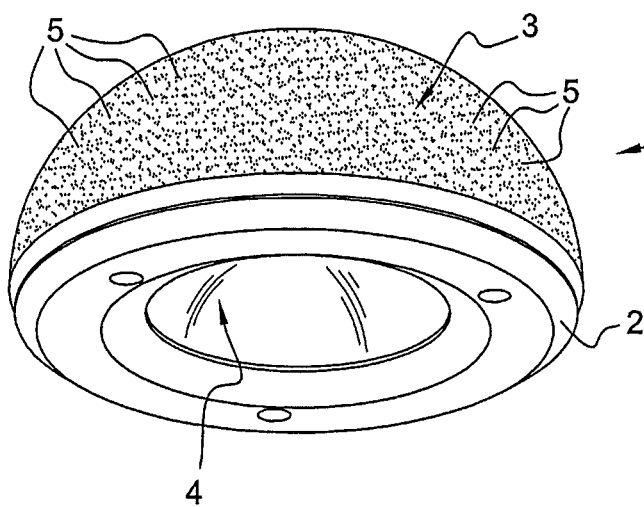
FIG. 1 is a perspective view of an orthopaedic implant in accordance with the invention.

FIG. 1 illustrates an orthopaedic implant 1, which forms an acetabular cup for hip prosthesis. In other words, the orthopaedic implant 1 is an acetabular implant. The orthopaedic implant 1 includes a substrate 2 comprising at least one polymer plastic material. In the example of the figures, the orthopaedic implant 1 includes only the substrate 2, which is in one-piece.

The polymer plastic material forming the substrate 2 is a high-density polyethylene (HDPE). In practice, this polymer plastic material may be selected in the group consisting of a high-density polyethylene (HDPE), a highly cross-linked polyethylene (XLPE), a polyurethane and a polyether ether ketone (PEEK).

Figure 2:
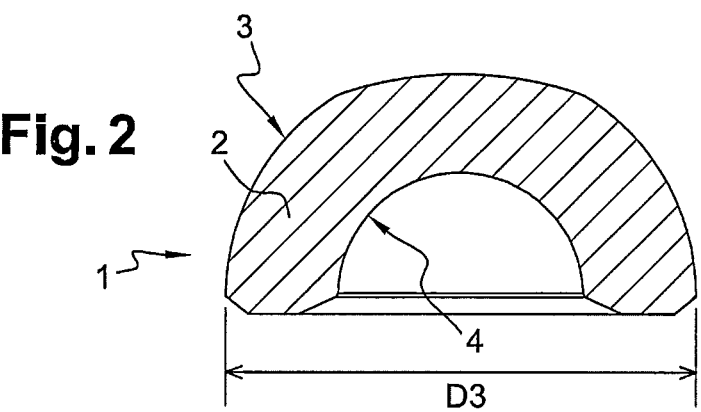
FIG. 2 is a perspective view, truncated along plane II of FIG. 1 and along an angle different from FIG. 1, of the orthopaedic implant of FIG. 1.

The substrate 2 has an outer surface 3 which is intended to be secured to a bone tissue belonging to the non represented iliac bone. As shown in FIG. 2, the outer surface 3 has generally the shape of a half-spheroid or even a half-sphere, intended to be embedded in the iliac bone. The outer surface 3 has a diameter D3 of about 50 mm. Alternatively, the diameter of the outer surface can be selected between 40 mm and 70 mm.

The substrate 2 further has an inner surface 4 located opposite to the outer surface 3. The inner surface 4 forms an acetabular cup surface, for the articulation of a non represented femoral head.

Figure 3:
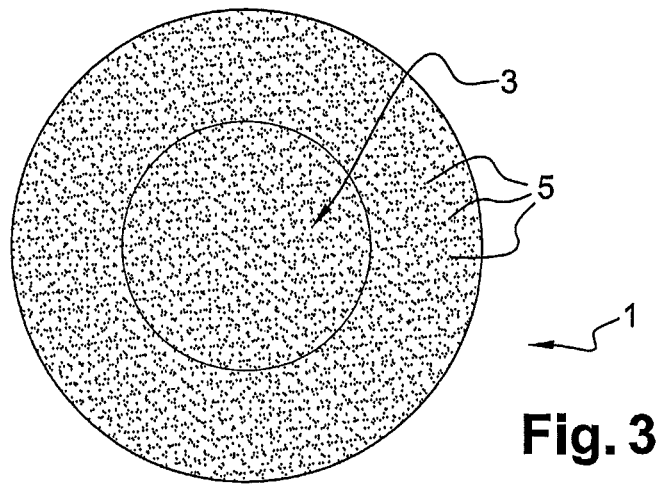
FIG. 3 is a top view of the orthopaedic implant of FIG. 1.

As shown in FIG. 3, the outer surface 3 is partially covered with particles 5 of a metallic material composed here of pure titanium. In practice, the or each metallic material may be a titanium alloy, hence a material comprising titanium and another material, metallic or not, for example chromium, cobalt and stainless steel such as the 316LVM steel. For example, such alloys are defined in the ISO 5832 standard.

A portion of the outer surface 3 is not covered with the particles 5. The surface area of this outer surface 3 portion not covered with the particles 5 represents about 25% of the total surface area of the outer surface 3. In other words, the particles 5 cover about 75% of the total surface area of the outer surface 3. In the example of the figures, the total surface area of the outer surface 3 is about 3930 mm$^2$, while the surface area of this non-covered outer surface 3 portion.

As shown in FIGS. 4 and 5, the particles 5 mainly comprise primary particles 51 and secondary particles 52. In the example of the figures, the primary particles 51 and the secondary particles 52 are composed of the same metallic material, pure titanium.

The number of primary particles 51 represents substantially between 5% and 50%, preferably between 10% and 30%, of the sum of the number of primary particles 51 and the number of secondary particles 52, that is to say about the total number of particles 5. As a corollary, the number of secondary particles 52 represents substantially between 95% and 50%, preferably between 70% and 30%, of the sum of the number of primary particles 51 and the number of secondary particles 52.

In the example of the figures, the total mass of primary 51 and secondary 52 particles may be for example comprised between 4 g and 20 g.

The primary particles 51 have a grain size ranging substantially from 200 μm to 500 μm. The secondary particles 52 have a grain size ranging substantially from 90 μm to 125 μm.

In practice, the primary particles 51 have a grain size ranging substantially from 180 μm to 600 μm. In practice, the secondary particles 52 have a grain size ranging substantially from 70 μm to 145 μm.

The primary particles 51 and the secondary particles 52 are distributed in a relatively uniform manner over the outer surface 3. Thus, the primary interstices between primary particles 51 have approximately equal surface areas. These primary interstices house the secondary particles 52.

As illustrated in FIG. 6, a method in accordance with the invention, for manufacturing the orthopaedic implant 1, comprises the steps of:
  placing the substrate 2 in a mold 101, which allows in particular performing the manufacturing method under a controlled atmosphere;
  heating the outer surface 3 to a softening temperature of the high-density polyethylene (HDPE);
  partially covering the outer surface 3 with primary particles 51, so that the primary particles 51 are distributed in a relatively uniform manner over the outer surface 3;
  pressing a heated die 102 against the outer surface 3, so as to secure the primary particles 51 to the outer surface.

Furthermore, as shown in FIG. 6, such a manufacturing method comprises the steps of:
  partially covering the outer surface 3 with secondary particles 52, so that the secondary particles 52 are distributed in a relatively uniform manner over the outer surface 3; and
  pressing the heated die 102 against the outer surface 3, so as to secure the secondary particles 52 to the outer surface 3.

In the method in accordance with the invention, the step of covering the outer surface 3 with the primary particles 51 is performed before the step of covering the outer surface 3 with the secondary particles 52.

Alternatively, the primary particles and the secondary particles may be mixed beforehand to form a homogeneous powder. Thus, the step of covering the outer surface with the primary particles may be performed simultaneously in the step of covering the outer surface with the secondary particles.

The step of covering the outer surface with the primary particles and the step of covering the outer surface with the secondary particles are performed by putting in contact in the enclosed volume of the mold 101 which is pressurized and heated at a temperature lower than the melting temperature of the polymer plastic material. To this end, dies 102 and 103 may exert pressures P102 and P103 on the mold 101. A spacer 104 distributes the pressures P102 and P103.

In service, the orthopaedic implant 1 forms an acetabular cup for hip prosthesis or acetabular implant. The orthopaedic implant 1 is secured to a bone tissue belonging to the non represented iliac bone. The articulation of the femoral head is made on the inner surface 4.

The invention claimed is:

1. An orthopaedic implant, including:
  at least one substrate comprising at least one polymer plastic material that provides a polymer-plastic outer surface configured to be secured to a bone tissue; and
  particles of at least one metallic material comprising titanium partially covering the outer surface such that the surface area of the outer surface portion that is not covered with the particles is between 15% and 30% of the total surface area of the outer surface, wherein:
  the particles comprise primary particles and secondary particles;
  the primary particles have a grain size ranging from 180 μm to 600 μm;
  the primary particles are distributed over the outer surface such that primary interstices between the primary particles have surface areas that are approximately equal in which each surface area is within ±20% of a median surface area for the primary interstices;
  the secondary particles have a grain size ranging from 70 μm to 145 μm; and
  the primary particles and the secondary particles are distributed in a relatively uniform manner over the outer surface such that the secondary particles are present within the primary interstices between the primary particles.

2. The orthopaedic implant according to claim 1, wherein the polymer plastic material is selected from the group consisting of a polyethylene (PE), an ultra-high molecular weight polyethylene (UHMW-PE), a highly cross-linked polyethylene (XLPE), an E-vitaminized polyethylene, a polyurethane and a polyether ether ketone (PEEK).

3. The orthopaedic implant according to claim 1, wherein the or each metallic material is selected from the group consisting of pure titanium and alloys of titanium, chromium, cobalt and stainless steel.

4. The orthopaedic implant according to claim 1, wherein the primary particles and the secondary particles are composed of the same metallic material.

5. The orthopaedic implant according to claim 1, wherein the number of primary particles is between 5% and 50% of the sum of the number of primary particles and the number of secondary particles.

6. The orthopaedic implant according to claim 1, wherein the outer surface has generally the shape of a spheroidal portion.

7. The orthopaedic implant according to claim 1, wherein the substrate is a one-piece single substrate formed entirely from the polymer plastic material.

8. The orthopaedic implant according to claim 1, wherein the primary particles have a grain size ranging from 200 μm to 500 μm, and the secondary particles have a grain size ranging from 90 μm to 125 μm.

9. The orthopaedic implant according to claim 1, wherein the surface area of the outer surface portion that is not covered with the particles is between 20% and 25% of the total surface area of the outer surface.

10. The orthopaedic implant according to claim 1, wherein the number of primary particles is between 10% and 30% of the sum of the number of primary particles and the number of secondary particles.

11. The orthopaedic implant according to claim 1, wherein the outer surface has the shape of a half-sphere.

12. The orthopaedic implant according to claim 1, wherein the orthopaedic implant is an acetabular cup for a hip prosthesis.

13. The orthopaedic implant according to claim 1, wherein the outer surface is stepless.

14. A method of manufacturing the orthopaedic implant according to claim 1, the method comprising the steps of:
  heating the outer surface to a softening temperature of the polymer plastic material;
  partially covering the outer surface with the primary particles such that the primary interstices between the primary particles have surface areas that are approximately equal in which each surface area is within ±20% of the median surface area for the primary interstices;
  pressing a heated die against the outer surface so as to secure the primary particles to the outer surface;
  partially covering the outer surface with the secondary particles in a relatively uniform manner over the outer surface such that the secondary particles are present within the primary interstices between the primary particles; and pressing the heated die against the outer surface so as to secure the secondary particles to the outer surface.

15. The method according to claim 14, wherein the step of partially covering the outer surface with the primary particles is performed before the step of partially covering the outer surface with the secondary particles.

16. The method according to claim 14, wherein the step of partially covering the outer surface with the primary particles and the step of partially covering the outer surface with the secondary particles are performed in an enclosed volume that is pressurized and heated at a temperature lower than the melting temperature of the polymer plastic material.

17. The method according to claim 14, wherein the primary particles have a grain size ranging from 200 μm to 500 μm, and the secondary particles have a grain size ranging from 90 μm to 125 μm.

18. The method according to claim 14, wherein the orthopaedic implant is an acetabular cup for a hip prosthesis.

* * * * *